United States Patent [19]
Ashraf-Khorassani et al.

[11] Patent Number: 5,453,198
[45] Date of Patent: Sep. 26, 1995

[54] METHOD FOR COLLECTING ANALYTE AND AN ORIFICE FOR REDUCING PRESSURE OF A FLUID

[75] Inventors: Mehdi Ashraf-Khorassani, Pittsburgh; Gregory Shogan, North Huntingdon; Raymond K. Houck, Oakmont, all of Pa.

[73] Assignee: Suprex Corporation, Pittsburgh, Pa.

[21] Appl. No.: 993,295

[22] Filed: Dec. 21, 1992

Related U.S. Application Data

[62] Division of Ser. No. 662,255, Feb. 28, 1991, Pat. No. 5,205,987.

[51] Int. Cl.⁶ ................................................. B01D 11/04
[52] U.S. Cl. ............................................. 210/634; 210/137
[58] Field of Search ............................ 137/802; 251/367, 251/118; 210/634, 198.2, 137

[56] References Cited

U.S. PATENT DOCUMENTS

| | | |
|---|---|---|
| 2,500,750 | 3/1950 | Halenza . |
| 3,565,192 | 2/1971 | McLarty ..................... 175/246 |
| 4,597,943 | 7/1986 | Sugiyama et al. . |
| 4,892,654 | 1/1990 | Nickerson . |
| 4,962,275 | 10/1990 | Bruno . |
| 4,984,602 | 1/1991 | Saito et al. . |
| 5,009,778 | 4/1991 | Nickerson et al. . |
| 5,087,360 | 2/1992 | Wright et al. ............ 210/198.2 |
| 5,094,741 | 3/1992 | Frank et al. . |
| 5,094,753 | 3/1992 | Allington et al. . |
| 5,151,178 | 9/1992 | Nickerson et al. . |
| 5,160,624 | 11/1992 | Clay et al. . |
| 5,173,188 | 12/1992 | Winter et al. . |
| 5,178,767 | 1/1993 | Nickerson et al. . |
| 5,180,487 | 1/1993 | Saito et al. . |

FOREIGN PATENT DOCUMENTS

| | | |
|---|---|---|
| 0438184 | 1/1987 | European Pat. Off. . |
| 1500168 | 12/1965 | Germany .......................... 251/118 |

*Primary Examiner*—Frank Spear
*Attorney, Agent, or Firm*—Ansel M. Schwartz

[57] ABSTRACT

An orifice which includes a housing having a low pressure side with a first bore hole and a second bore hole. The low pressure side has a first channel and a second channel in fluidic communication with the first bore hole and the second bore hole, respectively. The housing also has a high pressure side with a third bore hole. The orifice also includes an adapter which has a tip, a fourth bore hole and a third channel in fluidic communication therewith. The third channel has a constant diameter for maintaining an essentially constant pressure thereacross when pressure is applied thereto such that fluid flowing through the third channel does not solidify. The adapter is sealingly received by the third bore hole such that the third channel and the first channel align. Additionally, the housing includes an interface plate disposed in the housing between the third channel and the first channel. The plate sealingly receives the tip of the adapter and allows for flow to exist between the third channel and the first channel through a plate hole. A method for collecting analyte. The method includes the steps of providing analyte obtained from supercritical fluid extraction to a collection trap through a high pressure side of an orifice.

10 Claims, 3 Drawing Sheets

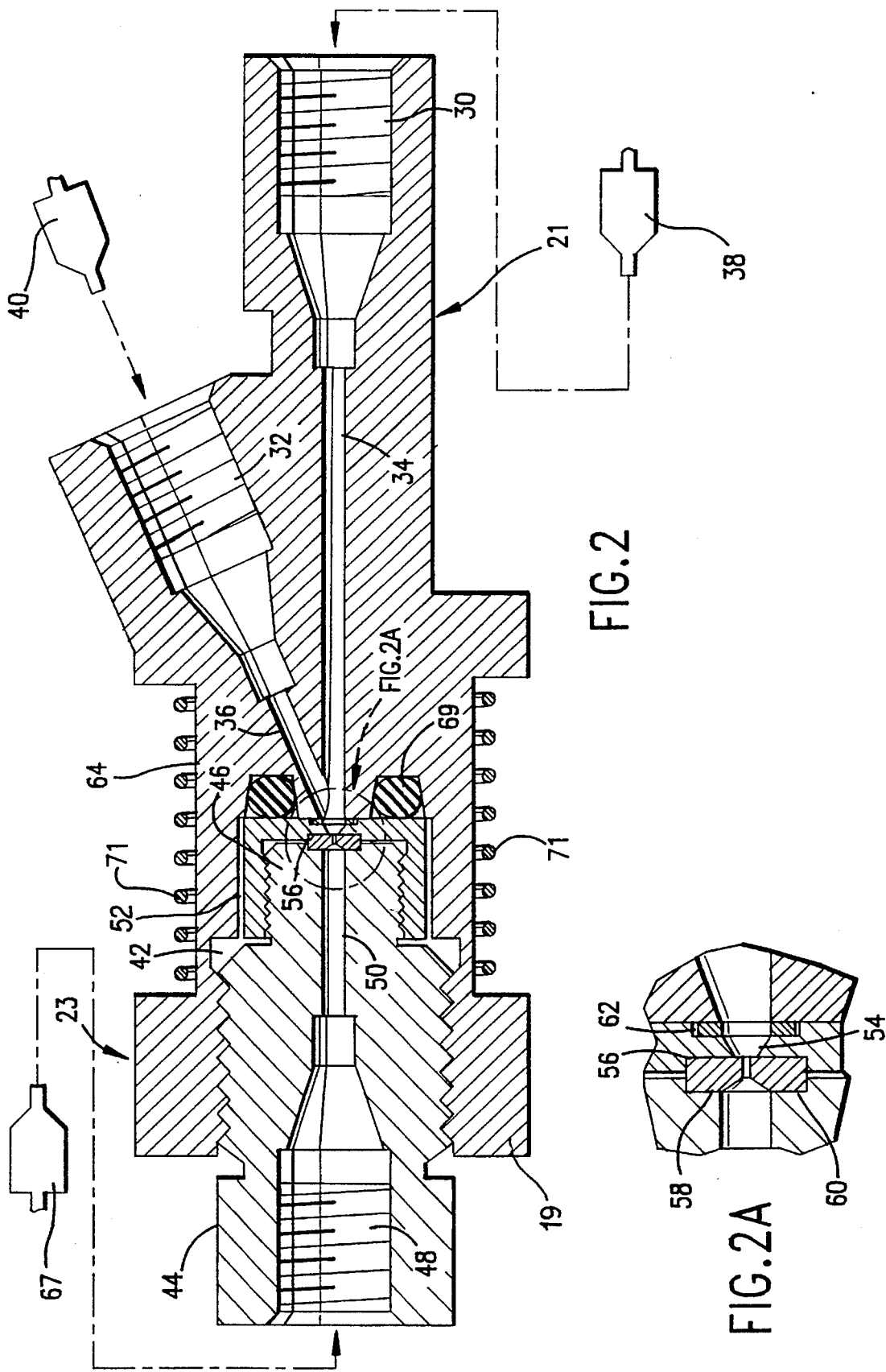

METHOD FOR COLLECTING ANALYTE AND AN ORIFICE FOR REDUCING PRESSURE OF A FLUID

This is a divisional of application Ser. No. 07/662,255 filed on Feb. 28, 1991, now U.S. Pat. No. 5,205,987.

FIELD OF THE INVENTION

The present invention is related to supercritical fluid extraction systems. More specifically, the present invention is related to an off-line supercritical fluid collection system having an orifice that allows essentially all analyte to pass therethrough.

BACKGROUND OF THE INVENTION

Supercritical fluid extraction (SFE) is used to analyze a sample. It offers a relatively rapid, simple and inexpensive technique to do the same. The basis of SFE is that the sample being analyzed is introduced to a fluid which is above its critical temperature and pressure. Such a fluid is otherwise known as a supercritical fluid. Supercritical fluids have favorable diffusivities and viscosites providing for good mass transfer characteristics. Their strength can be easily controlled, and since most are gases at ambient conditions, are easily workable. These are but a few of the advantages of supercritical fluids.

Typically, an SFE system is comprised of a pump which pumps the supercritical fluid to an extraction vessel where analytes are extracted from a sample matrix. The analytes are then transported to a collection device and the supercritical fluid, which is now no longer supercritical is vented. See "Analytical-Scale Supercritical Fluid Extraction" by S. B. Hawthorne, Analytical Chemistry, Vol. 62, No. 11, Jun. 1, 1990, pp. 633–642 and "Analytical Supercritical Fluid Chromatography and Extraction" by M. Lee and K. Marbides, Chromatography Conferences, Inc., 1990, incorporated by reference, for a general discussion of SPE.

As is apparent from the fact that a supercritical fluid is above its critical temperature and pressure, there needs to be an element of the SFE system which causes the supercritical fluid to be converted to a fluid at, for instance, ambient conditions. In general, some form of a flow restrictor is utilized between the extraction vessel and the collection vessel to accomplish this requirement. An SFE system is described in "Characterization of Sulfur Compounds in Spices Using SFE-GC-AED" by W. S. Miles and B. D. Quimby, *American Lab*, July 1990; and "Evolution of Coupled Supercritical Fluid Extraction—Cryogenic Collection—Supercritical Fluid Chromatography (SFE-CC-SFC) for Quantitive and Qualitative Analysis" by M. Ashrof-Khorossani, M. Kumar, D. Koebler, and G. Williams, Journal of Chromatographic Science, Vol. 28, Nov. 1990, pp. 599–604. In Miles, et al., supra, there is used a needle type restrictor which controls the flow of the fluid with analyte by varying the distance of the needle tip to an opening.

However, it is recognized that in order to maximize the transfer of analyte and fluid from high pressure to lower pressures as true a turbulent flow is desired thereacross. A restrictor which has steep internal tapers (decreasing from 50 μm to less than 1 μm within less than 1 mm, leading to a pinhole opening produces nearly turbulent flow and is very desirable. See "Linear Velocity Control in Capillary Supercritical Fluid Chromatography by Restrictor Temperature Programming" by A. Berger and C. Toney, Journal of Chromatography, 465 (1989) pp. 157–167. Also, see "Performance of Capillary Restrictors in Supercritical Fluid Chromatography" by R. Smith, J. Fulton, R. Peterson, A. Kopwa and B. Wright, Anal. Chem. 1986, 58, 2057–2064; and "Integral Pressure Restrictor for Capillary SFC" by E. Guthaie and H. Schwartz, Journal of Chromatographic Science, Vol. 24, June 1986, 236–241 which discuss the general importance of restrictors.

Also, see U.S. Pat. No. 3,827,859 which discloses a diaphragm arrangement for various pressure gradients thereacross in a flame ionization detector.

The present invention provides an orifice in an off-line SFE system that allows essentially all analyte to be gathered. The off-line feature of the present invention allows the analyte gathered to be taken to a remote location for desired testing.

SUMMARY OF THE INVENTION

The present invention pertains to an off-line collection system for use with supercritical fluid extraction. The system is comprised of means for collecting analyte associated with the supercritical fluid extraction. The system is additionally comprised of an orifice for controlling flow of analyte to the collecting means. The orifice converts analyte at a high pressure to a lower pressure. The orifice has a high pressure side which receives said high pressure analyte, and a lower pressure side in fluidic communication with the high pressure side which receives said high pressure analyte after it has been converted to a lower pressure. The high pressure side is capable of transporting analyte thereacross without essentially any loss thereof to the low pressure side which is in fluidic communication with the collecting means. The analyte experiences essentially constant pressure as it is transported across the high pressure side. The system is also comprised of means for desorbing the analyte from the collection means. The desorbing means is in fluidic communication with the collecting means. In a preferred embodiment, the system includes means for purging the analyte. The purging means is in fluidic communication with the collecting means. Additionally, the collecting means preferably includes a collection trap in which analyte is gathered, and means for controlling the flow of analyte into the collection trap. The flow controlling means is in fluidic communication with the collection trap and the purging means. The flow control means preferably includes an orifice.

An orifice which includes a housing having a low pressure side with a first bore hole and a second bore hole. The low pressure side has a first channel and a second channel in fluidic communication with the first bore hole and the second bore hole, respectively. The housing also has a high pressure side with a third bore hole. Preferably, the high pressure side is at a pressure at supercritical pressure. The orifice also includes an adapter which has a tip, a fourth bore hole and a third channel in fluidic communication therewith. The third channel has a constant diameter for maintaining an essentially constant pressure thereacross when pressure is applied thereto such that fluid flowing through the third channel does not solidify. The adapter is sealingly received by the third bore hole such that the third channel and the first channel align. Additionally, the housing includes an interface plate disposed in the housing between the third channel and the first channel. The plate sealingly receives the tip of the adapter and allows for flow to exist between the third channel and the first channel through a plate hole. The interface plate preferably includes a flow hole through which essentially all of the fluid from the third channel flows to the first channel. Preferably, the flow hole has fixed permanent dimensions. A method for collecting analyte. The method includes the steps of providing analyte obtained from supercritical fluid extraction to a collection trap through a high pressure side of an orifice. The orifice converts the higher pressure analyte to lower pressure analyte and provides it to a low pressure side thereof. The orifice controls the flow of the analyte to a collection trap such that essentially no analyte is lost in the high pressure side of the orifice. Then there is the step of cryogenically cooling the analyte in the collection trap. Next there is the step of heating the cooled analyte in the collection trap within 90 seconds. Then there is the step of desorbing the analyte from the collection trap. Then there is the step of gathering the analyte.

BRIEF DESCRIPTION OF THE DRAWINGS

In the accompanying drawings, the preferred embodiments of the invention and preferred methods of practicing the invention are illustrated in which:

FIG. 2 is a schematic representation of a cross sectional view of an orifice.

DESCRIPTION OF THE PREFERRED EMBODIMENT

Figure 1:
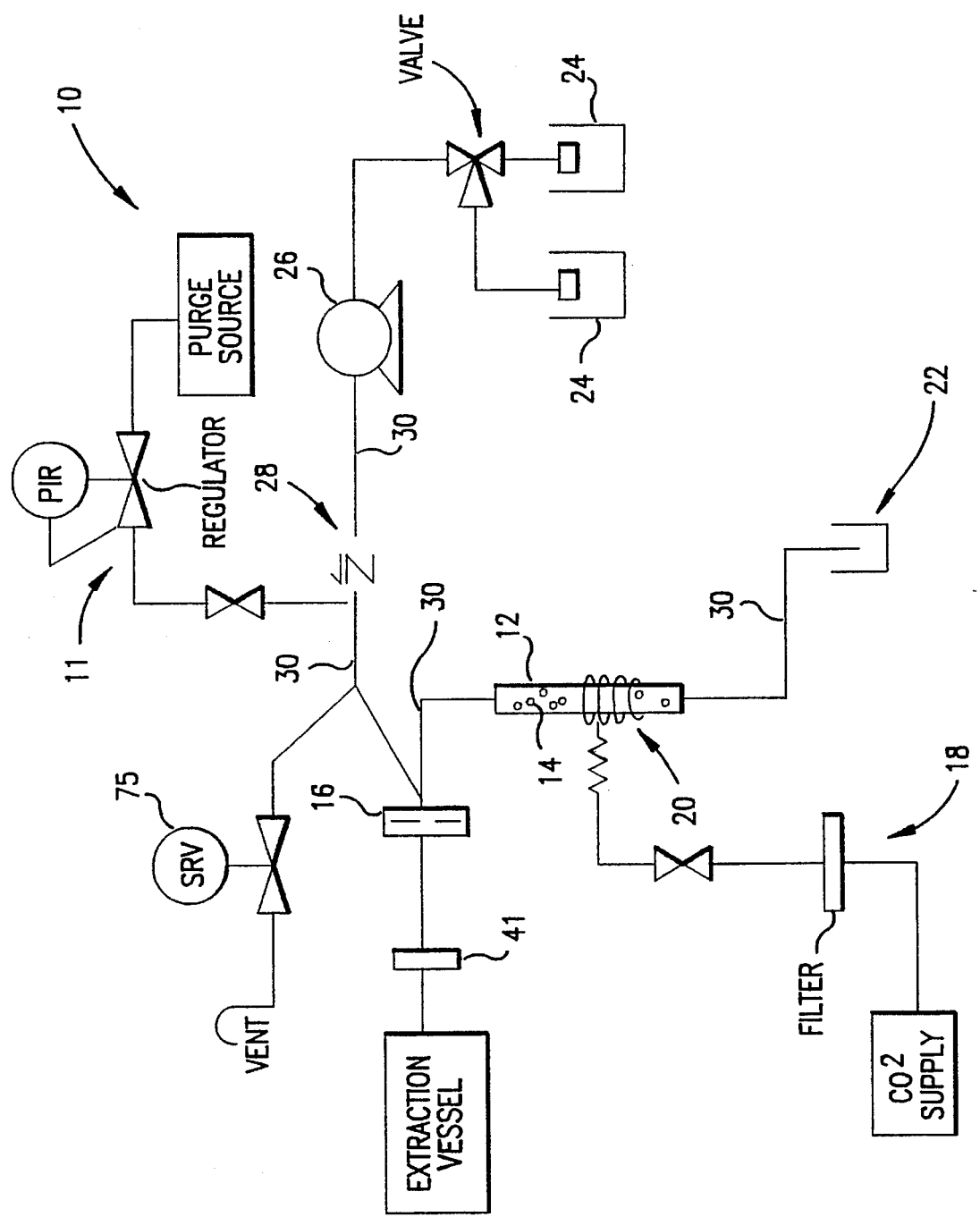
FIG. 1 is a schematic representation of an off-line supercritical fluid extraction collection system.

Referring now to the drawings wherein like reference numerals refer to similar or identical parts throughout the several views, and more specifically to FIG. 1 thereof, there is shown a schematic representation of an off-line collection system 10 for use with supercritical fluid extraction. The system 10 comprises means for collecting analyte associated with the supercritical fluid extraction. Additionally, the system 10 is comprised of means for desorbing the analyte from the collection means such that a greater than 90% collection efficiency is obtained. The desorbing means is in fluidic communication with the collecting means. Preferably, the system 10 includes means for purging the analyte. The purging means is in fluidic communication with the collecting means.

Preferably, the collecting means includes a collection trap 12 in which the analyte is gathered. The collection trap 12 can include beads 14 disposed therein to increase the surface area upon which the analyte can be gathered. The beads 14 can be steel balls, $C_{18}$, $NH_2$, CN, glass beads or silica. The pressure rating of the trap 12 should be at least 200 atmospheres. It is preferably made out of stainless steel, although essentially any good thermal conducting material which is nonreactive with the analyte that is able to withstand pressure can be used.

The system 10 is additionally comprised of an orifice 16 for controlling flow of analyte to the collection trap 12 as shown in FIG. 2. The orifice 16 converts analyte at a high pressure to a lower pressure. The orifice 16 has a high pressure side 19 which receives the high pressure analyte, and a low pressure side 21, in fluidic communication with the high pressure side 19, which receives the high pressure analyte after it has been converted to a lower pressure. The high pressure side 19 is capable of transporting analyte thereacross without essentially any loss thereof to the low pressure side 21. The analyte experiences essentially constant pressure as it is transported across the high pressure side 19. The low pressure side 21 is preferably in fluidic communication with the collection trap 12 and with the purging means.

The orifice 16 preferably has a housing 23 with the low pressure side 21 and the high pressure side 19. The low pressure side 21 preferably has a first bore hole 30 and a second bore hole 32. The low pressure side 21 has a first channel 34 and a second channel 36 in fluidic communication with the first bore hole 30 and the second bore hole 32, respectively. The first bore hole 30 is capable of receiving a first nozzle 38 and the second bore hole 32 is capable of receiving a second nozzle 40. The high pressure side 19 has a third bore hole 42.

The orifice 16 is also comprised of an adaptor 44 which has a tip 46, a fourth bore hole 48 and a third channel 50 in fluidic communication therewith. The third channel 50 is capable of maintaining essentially constant pressure thereacross when pressure is applied thereto such that fluid flowing through the third channel 50 does not solidify. The adaptor 44 is sealingly received by the third bore hole 42 such that the third channel 50 and the first channel 34 align.

The orifice 16 is also comprised of an interface plate 52 disposed in the housing 23 between the third channel 50 and the first channel 34. The plate 52 sealingly receives the tip 46 of the adaptor 44 and allows for a predetermined flow rate to exist between the third channel 50 and the first channel 34 through a plate hole 54.

Preferably, the plate 52 includes a first indentation 56 and a flow disc 58 having a flow hole 60 therethrough. The disc 58 is disposed in the first indentation 56 in communication with the adaptor 44 such that the flow hole 60 of the disc 58 aligns with the plate hole 54, the first channel 34 and third channel 50. The size of the flow hole 60 in the disc 58 dictates the flow rate between the third channel 50 and the first channel 34.

The plate 52 preferably has a second indentation 62 opposing the first indentation 56 and in communication with the first channel 34, with the plate hole 54 extending between the first indentation 56 and the second indentation 62. The orifice 16 preferably also includes a heating means, preferably a heating coil 71, in thermal communication with the housing 23 to heat the housing 23.

Figure 4:
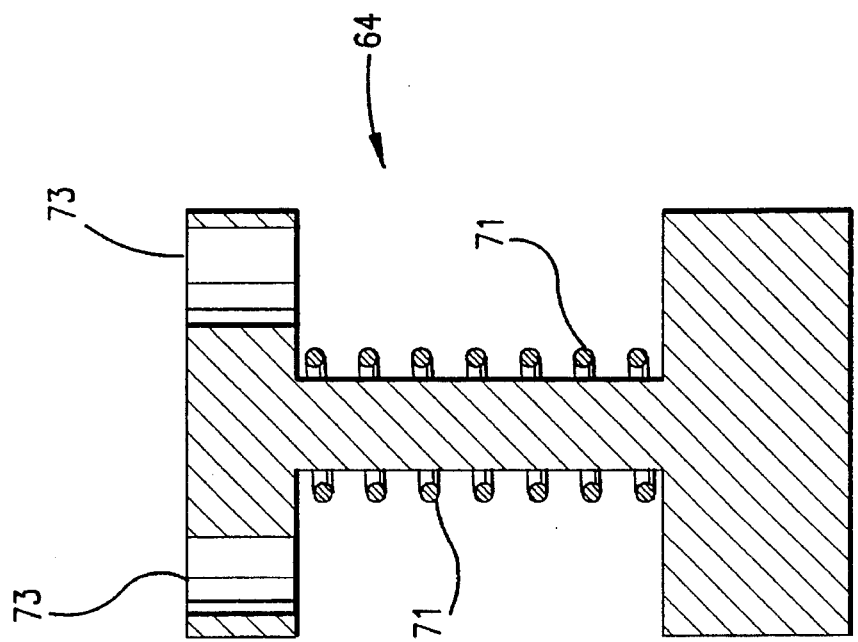
FIG. 4 is a section 4—4 view of FIG. 3.
Figure 3:
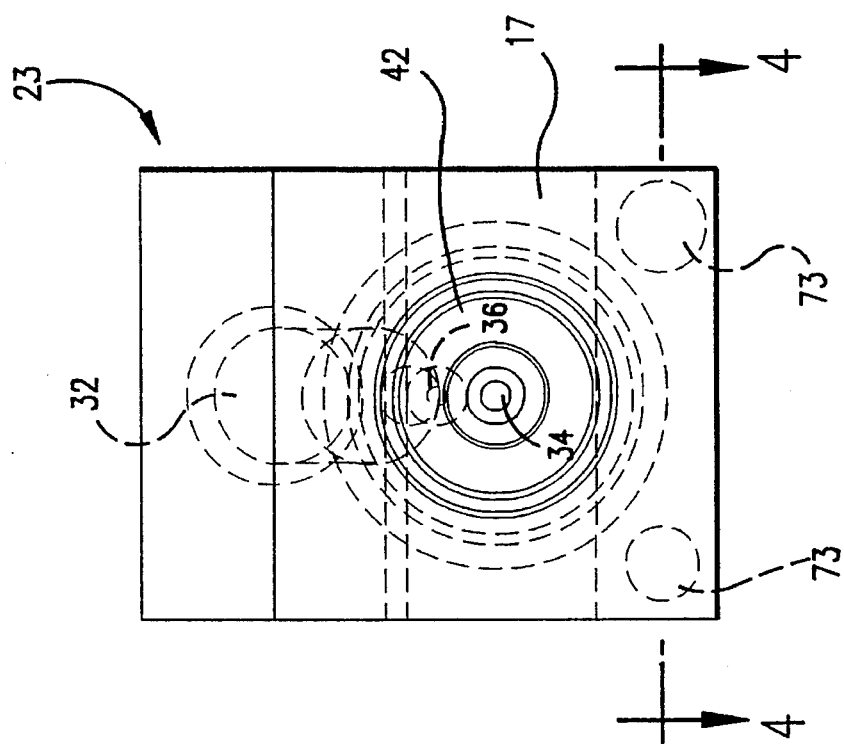
FIG. 3 is a schematic representation of a cross sectional high pressure side view of an orifice.

The housing 23 can have a slot 64 in which the heating means is disposed. Preferably, the slot 64 is positioned in proximity to the plate 52 and the heating coil 71 is disposed in the slot 64 such that the plate 52, first channel 34, second channel 36 and third channel 50 are heated thereby, as shown in FIG. 3 and FIG. 4.

The collection means preferably also includes means for cyrogenically cooling the collection trap 12 to at least $-5°$ C., and preferably $-40°$ C. and means for ballistically heating the collection trap 12 to, for instance, at least $30°$ C. from $-40°$ C. within 90 seconds and preferably 30 seconds. The cooling means and the heating means are in thermal communication with the collection trap 12.

The cooling means preferably includes means 18 for supplying liquid $CO_2$ about the collection trap 12 to cyrogenically cool the trap 12. The heating means preferably includes a resistance coil 20 disposed about the collection trap 12.

The collection means also preferably includes a vial 22 in fluidic communication with the collection trap 12. The desorbing means can include N liquid reservoirs 24, where N is an integer ≧1. The liquid reservoirs 24 hold liquid that desorbs analyte added in the collection trap 12 and transports it to the vial 22. The desorbing means also preferably includes means for pumping the liquid in the reservoir 24 to the collection trap 12. The pumping means is in fluidic communication with the reservoir 24 and the orifice 16. Preferably, the pumping means includes a pump 26 in fluidic communication with the liquid reservoir 24. The pumping means preferably also includes a check valve 28 in fluidic communication with the pump 26 in the orifice 16 such that liquid can only flow to the orifice 16 from the pump 26.

Preferably, the liquid reservoir 24 provides 2–5 mls of liquid to the collection trap 12. The fluidic communication between the above-described elements are obtained by the use of tubing 30 in the system 10 that is preferably stainless steel.

In the operation of the preferred embodiment, pyrene analyte is extracted from a matrix by known supercritical fluid extraction technique. The analyte which has dissolved in a solvent of supercritical $CO_2$ at 400 atmospheres and 100° C. temperature is provided to the adaptor 44 of the orifice 16 by way of 316 stainless steel tubing. The tubing passes through an in-line filter 41 which prevents plugging or clogging of the orifice 16. (Note the orifice 16 is essentially drawn to scale in FIG. 2. In the preferred embodiment, the housing 23 is 1.543 inches long. From FIG. 2, the remaining dimensions can be determined.)

The adaptor 44, which is on the high pressure side 17 of the housing 23 of the orifice 16 is threaded into a third bore hole 42 of the orifice 16 such that it is sealingly received by the orifice 16. The tip 46 of the adaptor 44 is threadingly received by an interface plate 52. The interface plate 52 has a plate hole 54 which provides fluidic communication between a first indentation 56 and a second indentation 62 in the plate 52. The first indentation 56 has disposed in it a disc 58 with a flow hole 60 therethrough. The flow hole is between 5 microns and 20 microns in diameter. The control of flow through the flow hole 60 results in a corresponding pressure drop across the plate 52. The plate hole 54 is aligned with the flow hole 60, the third channel 50 and the adaptor 44 such that analyte dissolved in supercritical $CO_2$ passes therethrough to the first channel 34 of the low pressure side 21 of the housing 23 of the orifice 16. After the $CO_2$ passes through the interface plate 52, it is no longer supercritical.

The steel tubing providing the fluidic connection from the supercritical fluid extraction device to the adaptor 44 is connected thereto with a third nozzle 67. The fourth bore hole 48 and the adaptor 44 is in fluidic communication with the third channel 50.

The third channel 50 is essentially a constant diameter throughout the adaptor 44. By having a constant diameter, there is essentially no loss of analyte due to a drop in pressure resulting in solidification of the analyte on the surface of the third channel 50. Consequently, analyte in the supercritical $CO_2$ flows from the third nozzle 67 through the third channel 50 and only at the flow hole 60 of the disc 58 does the analyte begin to experience a drop in pressure. The analyte passes through the flow hole 60 through the plate hole 54 and into the first channel 34 experiencing a drop in pressure. An o-ring 69 is seated on the low pressure side of the housing 23 and in contact with the plate 52 such that it seals the plate 52 with respect to the low pressure side 17 and prevents any solvent having analyte therein from escaping.

The low pressure side 21 of the orifice 16 is fluidically connected to the collection trap 12 by stainless steel tubing. The $CO_2$ with the analyte flows therethrough at a pressure of approximately 10 atmospheres or less.

The orifice 16 is maintained at essentially 40° C. with a heating coil 71 positioned about a slot 64 in the housing 23. A thermal couple in thermal contact with the heating coil 71 senses the temperature of the housing 23 and controls the amount of heat provided thereto with the coil 71. Wiring to provide electric current and information from and to the elements in the slot 64 extends through ports 73 in the housing 23 as shown in FIG. 3.

The collection trap 12 is stainless steel for good heat transfer and is capable of withstanding pressure up to 65 atmospheres. The trap 12 has an inside diameter of 4.6 millimeters, a ¼ inch outside diameter and is 7.5 centimeters long. The trap is filled with silanized glass beads of 100–120 mesh. The presence of the beads 14 increases the surface area upon which analyte can solidify as it passes through the collection trap 12. The collection trap 12 is cryogenically cooled with liquid $CO_2$. The collection trap 12 is able to be cooled within a two-minute period from ambient temperature to −50° C. The liquid $CO_2$ is provided by known techniques about the collection trap 12 and includes an on-off valve to deliver the cooling $CO_2$.

The analyte essentially in its entirety solidifies on the stainless steel tubing connecting the first channel 34 to the collection trap 12 and on the various surfaces in the collection trap 12.

After the analyte has been provided to the collection trap 12, the collection trap 12 is then ballistically heated from −50° C. to 40° C. within thirty seconds using a resistance coil 20. A pump 26 fluidically connected to a liquid reservoir 24 containing five milliliters of methylene chloride at atmospheric pressure is activated essentially at the same time that the collection trap 12 is ballistically heated and pumps the methylene chloride solvent. The solvent flows through a check valve 28 into the low pressure side 21 of the housing 23, through a second channel 36, and into the first channel 34 which is in fluidic communication with the second channel 36. The deabsorbant then is provided to the collection trap 12. The tubing that provides the fluidic connection liquid between the reservoir 24 to the high pressure side 21 of the housing 23 is made of stainless steel. The check valve 28 allows only the solvent to pass therethrough from the reservoir 24 but prevents any analyte that has passed through the orifice 16 from passing therethrough. It should be noted that analyte flowing to the check valve 28 may solidify along the interior surface of the second channel 36 and the tubing as possibly does the analyte passing through the first channel 34. However, since the solvent flows therealong, it gathers any analyte in the tubing and second channel 36 and eventually provides it to the collection trap 12 and subsequently to a vial 22. Thus, essentially no analyte is lost through this route.

The tubing fluidically connected to the check valve 28 is received by the second bore hole 32 in the housing 23 by way of a second nozzle 40. The second channel 36 is in fluidic communication with the second bore hole 32 such that any solvent flowing therealong enters the second channel 36 and flows to the first channel 34 which is in fluidic communication with the second channel 36. The juncture of the second channel 36 with the first channel 34 is essentially at the second indentation 62 of the plate 52. The second indentation 62 and plate hole 54 essentially form a conical shape. The angle of the conical shape is essentially of the same angle as the angle of the second channel 6 forms with respect to the first channel 34. This angle is approximately 29° with respect to the axis of the first channel 34. By having such a conical shape, the second indentation 62 and plate hole 54 eliminates the possibility of any solvent collecting in a dead spot and being lost. The flow hole 60 of the disc 58 is so small that essentially no solvent is lost therethrough.

Additionally, there is a safety relief valve 75 fluidically connected to the tubing downstream of the check valve 28. The safety relief valve 75 ensures that if there is a pressure buildup in excess of that desired, then the pressure is vented without damage to the system 10.

As the solvent flows through the collection trap 12 at essentially 2 milliliters per minute, the pyrene dissolves in the methylene chloride. The solvent continues through the collection trap 12 gathering the analyte, and then flows by way of tubing to a vial 22 where it is collected. The vial can be taken to a remote location, if desired, for further analyzation. Once the solvent has passed through the collection trap 12 and is collected by the vial 22, the tubing, the low pressure side 21 of the housing 23 and the collection trap 12 are purged with $N_2$ at approximately 50 PSIA and at ambient temperature to remove any residual traces of the liquid solvent.

The following are various tables of analytes collected with the system 10.

TABLE I

Off-Line Collection Efficiency in Dry Vial

| Compounds | Standard | Percent Recovery | |
|---|---|---|---|
| | | Run 1 | Run 2 |
| 1-methyl naphthalene | 100 | 6 | 6 |
| 2-methyl naphthalene | 100 | — | 4 |
| 1-methyl fluorene | 100 | 31 | 18 |
| Phenanthrene | 100 | 28 | 16 |
| Anthracene | 100 | 23 | 12 |
| Fluoranthene | 100 | 23 | 14 |
| Pyrene | 100 | 21 | 13 |
| Chrysene | 100 | 20 | 23 |

Methylene chloride is used as a solvent.

TABLE II

Off-Line Collection Efficiency with $CH_2Cl_2$ Solvent in Vial

| Compounds | Standard | Percent Recovery | |
|---|---|---|---|
| | | Run 1 | Run 2 |
| 1-methyl naphthalene | 100 | 22 | 19 |
| 2-methyl naphthalene | 100 | 23 | 19 |
| 1-methyl fluorene | 100 | 31 | 35 |
| Phenanthrene | 100 | 32 | 36 |
| Anthracene | 100 | 29 | 38 |
| Fluoranthene | 100 | 34 | 38 |
| Pyrene | 100 | 34 | 38 |
| Chrysene | 100 | 38 | 32 |

Methylene chloride is used as a solvent.

TABLE III

Off-Line Collection Efficiency Using Trap 12

| Compounds | Standard | Percent Recovery | |
|---|---|---|---|
| | | Run 1 | Run 2 |
| 1-methyl naphthalene | 100 | 87 | 94 |
| 2-methyl naphthalene | 100 | 87 | 93 |
| 1-methyl fluorene | 100 | 109 | 100 |
| Phenanthrene | 100 | 110 | 102 |
| Anthracene | 100 | 108 | 102 |
| Fluoranthene | 100 | 115 | 101 |
| Pyrene | 100 | 115 | 100 |
| Chrysene | 100 | 119 | 107 |

Trap 12 temperature during collection: −20° C.
Trap 12 temperature during wash: 40° C.
Methylene chloride is used as a solvent.

TABLE IV

Off-Line Collection Efficiency of Hydrocarbons in Trap 12

| Compounds* | Standard | Percent Recovery | |
|---|---|---|---|
| | | Run 1 | Run 2 |
| C10 | 100 | 15 | 0 |
| C11 | 100 | 27 | 7.5 |
| C12 | 100 | 60 | 25 |
| C14 | 100 | 74 | 50 |
| C15 | 100 | 81 | 65 |
| C16 | 100 | 87 | 81 |
| C17 | 100 | 89 | 90 |
| C18 | 100 | 90 | 91 |
| C20 | 100 | 89 | 90 |
| C24 | 100 | 99 | 96 |
| C28 | 100 | 96 | 96 |
| C32 | 100 | 97 | 94 |
| C36 | 100 | 88 | 85 |
| C40 | 100 | 94 | 90 |

Trap 12 temperature during collection: −20° C.
Trap 12 temperature during wash: 40° C.
Hexane is used as the solvent.

TABLE V

Off-Line Collection Efficiency of Hydrocarbons in Trap 12

| Compounds* | Standard | Percent Recovery | |
|---|---|---|---|
| | | Run 1 | Run 2 |
| C10 | 100 | 69 | 70 |
| C11 | 100 | 72 | 71 |
| C12 | 100 | 75 | 73 |
| C14 | 100 | 79 | 80 |
| C15 | 100 | 83 | 81 |
| C16 | 100 | 86 | 88 |
| C17 | 100 | 88 | 90 |
| C18 | 100 | 88 | 91 |
| C20 | 100 | 88 | 95 |
| C24 | 100 | 90 | 90 |
| C28 | 100 | 87 | 92 |
| C32 | 100 | 88 | 89 |

TABLE V-continued

Off-Line Collection Efficiency of Hydrocarbons in Trap 12

| | | Percent Recovery | |
|---|---|---|---|
| Compounds* | Standard | Run 1 | Run 2 |
| C36 | 100 | 81 | 89 |
| C40 | 100 | 88 | 95 |

Trap 12 temperature during collection: −45° C.
Trap 12 temperature during wash: 40° C.
Hexane is the solvent.

TABLE VI

Off-Line Collection Efficiency of Pesticides Using Trap 12

| Compounds* | Standard | % Recovery |
|---|---|---|
| Gamma-BHC | 100 | 106 |
| Heptachlor | 100 | 70 |
| Aldrin | 100 | 93 |
| Heptachlor Epoxide | 100 | 117 |
| Endosulfan 1 | 100 | 94 |
| 4,4'-DPT | 100 | 99 |
| Endrin Aldehyde | 100 | 85 |
| Methoxychlor | 100 | 103 |

*Concentration: 6 to 15 nanogram/compound
Trap 12 temperature during collection: −30° C.?
Trap 12 temperature during wash: 40° C.
Methanol is the solvent.

TABLE VII

Off-Line Collection Efficiency of Phenols in Trap 12

| | | Percent Recovery | |
|---|---|---|---|
| Compounds* | Standard | Run 1 | Run 2 |
| 2-chlorophenol | 100 | 48 | 43 |
| 2-nitrophenol | 100 | 59 | 67 |
| 2,4,6,-Trichlorophenol | 100 | 73 | 88 |
| 4-nitrophenols | 100 | 83 | 110 |
| 4,6,-Dinitrophenol | 100 | 86 | 112 |
| Pentachlorophenol | 100 | 80 | 108 |

*Concentration: 400 ug/compound
Trap temperature during collection: −30° C.
Trap temperature during wash: 40° C.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for collecting analyte comprising the steps of:

providing analyte obtained from supercritical fluid extraction to a collection trap through a high pressure side of an orifice, said orifice converting the high pressure analyte to lower pressure analyte and providing it to a low pressure side thereof, said orifice controlling the flow of the analyte to a collection trap such that essentially no analyte is lost in the high pressure side of the orifice;

cryogenically cooling the analyte in the collection trap;

heating the cooled analyte in the collection trap within 90 seconds;

desorbing the analyte from the collection trap; and gathering the analyte.

2. The method of claim 1 wherein the desorbing step includes the step of introducing liquid into the collection trap via the low pressure side of the orifice to transport the analyte out of the collection trap.

3. The method of claim 2 including after the gathering step, the step of purging the collection trap.

4. An orifice comprising:

a housing having a low pressure side with a first bore hole and a second bore hole, said low pressure side having a first channel and a second channel in fluidic communication with the first bore hole and the second bore hole, respectively, said housing having a high pressure side with a third bore hole;

an adapter which has a tip, a fourth bore hole and a third channel in fluidic communication therewith, said third channel having a constant diameter for maintaining an essentially constant pressure thereacross when pressure is applied thereto such that fluid flowing through the third channel does not solidify, said adapter sealingly received by said third bore hole such that said third channel and said first channel align; and an interface plate disposed in the housing between the third channel and the first channel, said plate sealingly receiving said tip of said adapter and allowing for flow to exist between the third channel and the first channel through a plate hole, said interface plate comprising a flow hole through which essentially all of the fluid from the third channel flows to the first channel, said flow hole having fixed permanent dimensions.

5. An orifice as described in claim 4 wherein the plate includes a first indentation and a flow disc having the flow hole therethrough, said disc disposed in the first indentation and in communication with the adapter such that the flow hole of the disc aligns with the plate hole, first channel and third channel and the size of the flow hole in the disc dictates the flow rate between the third channel and the first channel.

6. An orifice as described in claim 5 wherein the plate has a second indentation opposing the first indentation and in communication with the first channel, with the plate hole extending between the first indentation and the second indentation.

7. An orifice as described in claim 6 including heating means in thermal communication with said housing to heat the housing.

8. An orifice as described in claim 7 wherein the housing has a slot in which the heating means is disposed.

9. An orifice as described in claim 8 wherein the heating means includes a heating coil, the slot is positioned in proximity to the plate and the heating coil is disposed in the slot such that the plate, first channel, second channel and third channel are heated thereby.

10. An orifice comprising:

a housing having a low pressure side with a first bore hole and a second bore hole, said low pressure side having a first channel and a second channel in fluidic communication with the first bore hole and the second bore hole, respectively, said first bore hole capable of receiving a first nozzle and said second bore hole capable of receiving a second nozzle, said low pressure side being at a pressure below supercritical pressure; said housing having a high pressure side with a third bore hole, said high pressure side being at a pressure at supercritical pressure;

an adapter which has a tip, a fourth bore hole and a third channel in fluidic communication therewith, said third channel maintaining an essentially constant pressure thereacross when pressure is applied thereto such that fluid flowing through the third channel does not solidify, said adapter sealingly received by said third bore hole such that said third channel and said first channel align; and an interface plate disposed in the housing between the third channel and the first channel, said plate sealingly receiving said tip of said adapter and allowing for a predetermined flow rate to exist between the third channel and the first channel through a plate hole.

* * * * *